(12) United States Patent
Kushnir (10) Patent No.: US 6,500,200 B1
(45) Date of Patent: *Dec. 31, 2002

(54) HEAT EXCHANGER GARMENT

(75) Inventor: Igal Kushnir, Pardes Hana (IL)

(73) Assignee: M.T.R.E. Advanced Technologies Ltd., Caesaria (IL)

(*) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/582,849

(22) PCT Filed: Sep. 1, 1999

(86) PCT No.: PCT/IL99/00474

§ 371 (c)(1),
(2), (4) Date: Aug. 14, 2000

(87) PCT Pub. No.: WO00/62726

PCT Pub. Date: Oct. 26, 2000

(30) Foreign Application Priority Data

Apr. 15, 1999 (IL) .................................................. 129465

(51) Int. Cl.$^7$ .................................................. A61F 2/00
(52) U.S. Cl. ........................ 607/104; 607/108; 607/112; 165/46
(58) Field of Search ............................ 607/96, 99, 104, 607/108, 112, 109, 110, 111, 107; 165/46; 5/421, 422; 126/204; 602/2, 14

(56) References Cited

U.S. PATENT DOCUMENTS

| 3,744,053 A | * | 7/1973 | Parker et al. .................. 2/2.16 |
| 4,149,541 A | * | 4/1979 | Gammons et al. .......... 607/104 |
| 5,662,695 A | * | 9/1997 | Mason et al. .................. 607/96 |
| 5,683,439 A | * | 11/1997 | Jensen ......................... 607/104 |
| 5,749,109 A | * | 5/1998 | Kappel ........................... 5/423 |
| 5,891,187 A | * | 4/1999 | Winthrop et al. ............. 607/96 |
| 6,113,626 A | * | 9/2000 | Clifton et al. ................ 607/96 |

* cited by examiner

Primary Examiner—Linda C. M. Dvorak
Assistant Examiner—Kenneth G Schopfer
(74) Attorney, Agent, or Firm—Gary M. Nath; Todd L. Juneau; Joshua B. Goldberg (57) ABSTRACT

A heat exchanger for use in controlling subject's body temperature during a medical procedure comprises a flexible garment adapted for enveloping portions of the subject's body surface with dedicated sections for enveloping different body parts. Defined within the garment is a continuous, fluid tight space, wherein a flow path for heat-control fluid is defined between fluid inlet and fluid outlet. The inner faces of the garment's internal and external layers are made of a heat-weldable material and are point-welded to one another at a plurality of locations throughout the garment with a distance between two adjacent points being between about 8 to about 20 mm.

27 Claims, 8 Drawing Sheets

HEAT EXCHANGER GARMENT

FIELD OF THE INVENTION

The present invention relates to a heat exchanger which is intended to be applied onto a subject's body for controlling the subject's body temperature during medical procedure.

BACKGROUND OF THE INVENTION AND PRIOR ART

There are a variety of medical procedures in which a subject's body temperature has to be controlled. For example, during open heart surgery, the body temperature has to be controllably reduced to about 35° C. and then at the end of the operation increased back to normal body temperature. Furthermore, under general anesthesia, the natural physiological mechanisms which operate to maintain a body temperature may fail, and the problem becomes particularly acute in cases where exposed internal body organs come into contact with the ambient air which results in excessive heat loss. The problem is further aggravated by the fact that operation rooms are very often heavily cooled. Following surgical procedure, it may take some time until the body acquires back its ability to control its temperature.

Similarly as human subjects, the problem of controlling body temperature is also experienced during surgical procedures performed on animals.

Overall, controlling the body temperature is one of the serious problems facing the medical staff when performing operations.

U.S. Pat. No. 4,844,072, describes a system which may be used in thermal therapy and which includes a thermal pad with internal channels for carrying a temperature-control liquid therethrough. A thermal bandage which achieves a similar purpose is described in U.S. Pat. No. 4,962,761 through which heat control liquid is circulated when placed in contact with the body. In accordance with this patent, several such matters may be placed in series and fitted into a planar array or into a garment.

U.S. Pat. No. 5,269,369 discloses a temperature regulation system for human body which makes use of heat pipes which are incorporated into a garment, which distributes energy to and from portions of the human body.

A tube laminated heat transfer article for placing against a human body for transfer heat to or from the human body is disclosed in U.S. Pat. No. 5,755,275. A heating and/or cooling pad having the shape of the human body which is placed beneath the patient to allow heat or cold to radiate upwards is disclosed in U.S. Pat. No. 5,785,716.

MicroClimate Systems Inc., Stanford, Mich., U.S.A., markets a series of portable personal cooling systems (sold under the trademarks KOOLVEST, KOOLJACKET, KOOLBAND, KOOLPAID and others) which are intended for use by healthy persons who perform a physical activity in a hot environment (see Internet http://www.microclimate.com/prodline.html or http://www.microclimate.com/work.html). The system consists of a garment (it may be a vest, jacket, skull cap, a cervical collar, etc.) with tubing embedded therein in which water flows propelled by a battery-powered pump. Water passes through ice or through a cooling device before entering the tubing within the garment. The user can control the pump rate, the temperature, etc. A similar product line is also provided by Mallinckrodt Inc., St. Louis, Mo., U.S.A. (see the Internet at http://www/mallinckrodt.com/ccd) and others.

GENERAL DESCRIPTION OF THE INVENTION

In accordance with the invention, a heat exchanger in the form of a garment which is highly effective in transferring a heat to or from a subject's body in order to control the subject's body temperature has been developed. The invention thus provides, a heat exchanger for use in controlling a subject's body temperature during a medical procedure, comprising:

a flexible garment adapted for enveloping portions of the subject's body surface, the garment having dedicated sections for enveloping different body parts which comprise a torso section for enveloping substantial portions of the subject's torso and one or more extremity sections for enveloping portions of one or more of the individual's extremities;

a fastening arrangement for retaining each section in an enveloping state;

fluid-tight space defined between an internal, body-facing layer of the garment and an external layer and between fluid tight edges of the garment, the faces of both layers lining said space being attached to one another along lines defining a flow path between at least one fluid inlet and at least one fluid outlet to permit flow of fluid from the at least one inlet to the at least one outlet throughout essentially the entire garment for effective heat transfer to or from all parts of the garment;

the inner faces of the garment's internal and external layers are made of a heat-weldable material and are point welded to one another at a plurality of locations throughout the garment.

The fluid-tight space which is defined between the internal and the external layers of the garment, has typically a volume per unit area which is essentially the same throughout the entire garment. The point welds may be randomly distributed throughout the garment or may be arranged in an ordered array. A typical distance between two adjacent welded points in the garment is between about 8 to about 20 mm.

The garment is typically designed for working under fluid pressure of about 0.5–1.5 atmospheres. Typically, the space is formed such that under a pressure of this range the space's volume per unit area of the garment is in the range of about 1–3 liter/m$^2$ of garment surface.

A preferred heat exchanger in accordance with the invention is such wherein each of the internal and the external layers is constructed of two layers; namely the garment is a four-layered structure. This four-layered structure consists of two impermeble sheets lining said space overlaid by usually heavier reinforcing layers. All four layers are typically made of a heat-weldable material and are point welded to one another. The two innermost layers serve to define the fluid-tight space, while the outer layers reinforce the structure and allow the application of an increased internal fluid pressure, at times up to about 3 Atm without rupturing. Increase pressure may at times be of importance to ensure a certain level of flow of the heat-control fluid within the garment's inner space. The inner layers of the heat exchange may be made of a polyethylene-based material such as Metallocene (manufactured by Dow Chemicals) sheeting, typically but not restricted to about 20–50 $\mu$m thickness. The two outer layers are preferably somewhat hydrophilic to allow a certain degree of absorption of body and/or cleaning and disinfecting fluids and are also preferably soft to touch to ensure improved patient's comfort when contacting the skin. The outer layers may, for example, be made of a woven or non-woven spunbond fabric, e.g. made of polypropylene, having a characteristic weight of about 20 g/m² to about 50 g/m². The welding together of the four layers may be achieved, for example, by means of RF welding.

The heat exchanger having the aforementioned characteristics, is novel by itself (even when not formed into a garment as defined above), and forms an aspect of the present invention. The heat exchanger may be used for any application requiring a flexible heat exchanger with a relatively large heat exchange surface. A significant feature of the heat exchanger of this embodiment is that it is of low cost and high efficiency and has overall performance (heat exchange properties, flexibility, internal pressure resistance, and others) hitherto attained only with more complex and costly devices.

The heat transfer fluid is typically a liquid, e.g. water. A heat exchanger which is adapted for use with a liquid heat transfer fluid, typically made to circulate by a pump, is made with an internal flow resistance within the space such that under a pressure differential between the input and output of about 0.5 atmospheres, the flow rate through the garment will be in the range of about 0.5–2 liter/minute, typically about 1 liter/minute.

The garment is preferably designed such that each different section can be manipulated independently from other sections between an enveloping and a non-enveloping state. This has several advantages. For one, it allows easy accessibility to different parts of the body. Furthermore, this allows to use a single type of garment for different kinds of operations: for example in case of an operation performed on the subject's leg, the respective section will obviously be in the non-enveloping state while the other sections, namely those of the torso, the other leg, the arms, the neck, the head, etc., may be in an enveloping state. The feature of independent manipulation of the different sections between an enveloping and a non-enveloping state is typically achieved by emarginations in the garment's edges.

The garment may also have a modular design. For example, there may be a garment piece designed for the torso, a garment piece designed for the head, a garment piece designed for the legs or arms, etc. The different garment pieces may be combined to form a garment in a manner to meet specific needs.

The above feature allows to provide an effective cover of the human body by the garment sufficient to properly control the body temperature, for a wide variety of different medical procedures. One should also note that. effective heat transfer may be achieved regardless of the patient's position: whether he is placed lying on his back or whether he is placed with his back up or whether he is placed lying on his side, or even when positioned in a sitting position.

The heat exchanger of the invention is particularly useful in controlling the body temperature of a patient during surgery. The heat exchanger in accordance with the invention may be designed for all shapes and sizes of human subjects as well as for animals.

The invention will now be described in a non-limiting manner with respect to some specific embodiments shown in the annexed drawings.

DETAILED DESCRIPTION OF SPECIFIC EMBODIMENTS

Figure 1:
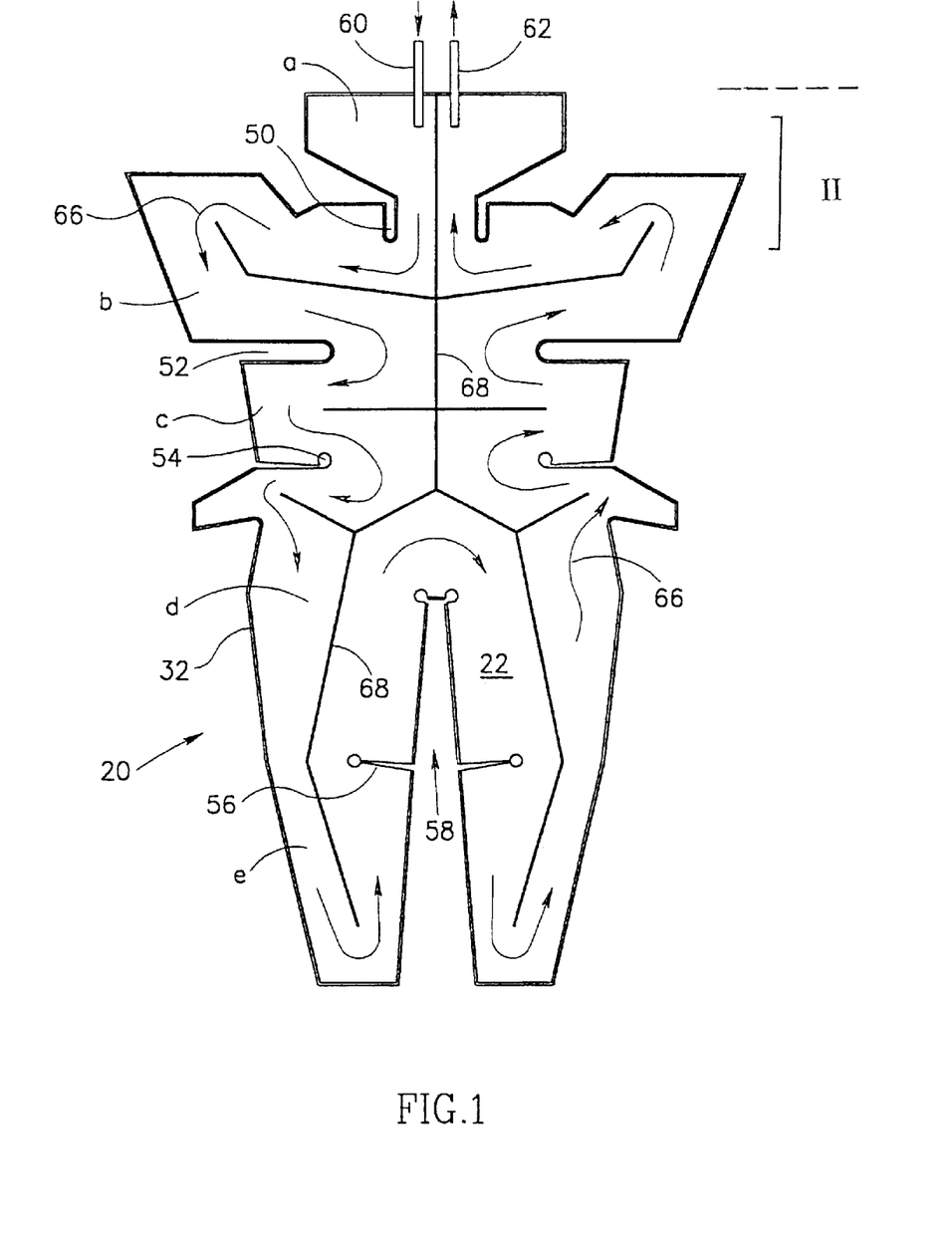
FIG. 1 is a top planar view of a garment in accordance with an embodiment of the invention.
Figure 2A:
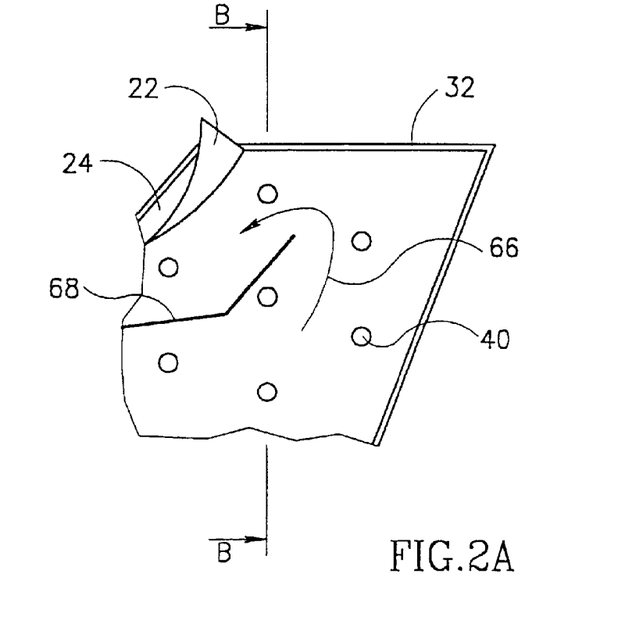
FIG. 2A is an enlargement of the region marked "II" in FIG. 1 with the internal and external layers being partially separated for illustrative purposes.
Figure 2B:
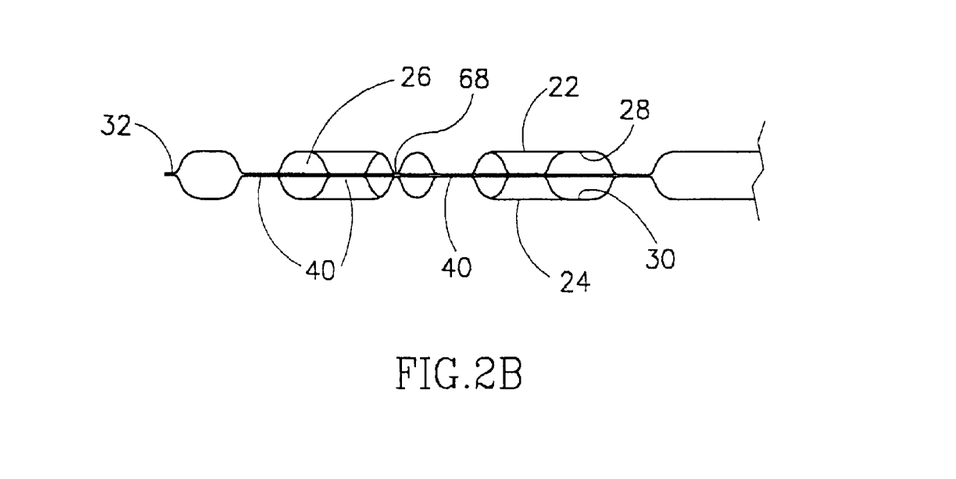
FIG. 2B is a cross-section through line B—B of FIG. 2A.

Reference is first being made to FIG. 1 showing a planar view of a garment generally designated 20 of which a part marked "II" in FIG. 1 is shown in a more enlarged view in FIG. 2A and of which a cross-section through lines B—B of FIG. 2A is shown in FIG. 2B. As can be seen in FIGS. 2A and 2B, the garment has an internal, body-facing layer 22 and an external layer 24 which define between them a fluid-tight space 26. Each of the layers 22, 24 is made from a thermoplastic material with a heat weldable, space-lining face 28, 30 (see FIG. 2B). The two layers are welded to one another in fluid tight manner at the edges 32.

The two layers 22, 24 are welded to one another at a plurality of weld points 40 seen in FIGS. 2A and 2B.

The weld points 40 cause a flow disturbance and consequently the flow of liquid through the garment (see description below) becomes uniform throughout the entire space of the flow path (see below).

The garment is symmetrical along a longitudinal midline which is a typical, but not exclusive case. Occasionally, garments for a variety of uses may also be made to be non symmetrical. As can be seen, the garment has a variety of dedicated sections a, b, c, d and e on both the left and right sides of the garment. The different sections are defined by the general shape of the garment as well as by emarginations 50, 52, 54, 56 and 58, part of which are in the form of lateral indentations while others are in the form of slits. Section a is intended for enveloping portions of the individual's neck and head, section b is for portions of the individual's arms, section c is for side portions of the individual's torso, section d is for the hip and thigh while section e is for the shin.

The garment is provided with a fluid inlet 60 and a fluid outlet 62, which in this specific embodiment are fitted into section a. As will no doubt be appreciated, this is a mere example and the outlet and inlet may be fitted into any other section, at times conveniently into section e at times conveniently into section c, etc. In addition, it is possible also to form the garment such that the fluid inlet will be in one section and the fluid outlet in another section of the garment.

In the garment, a flow path represented by a series of consecutive arrowed lines 66, is defined by means of flow path-defining weld lines, which are designated collectively by the numeral 68. These weld lines are formed by heat welding as generally known per se.

Figure 6:
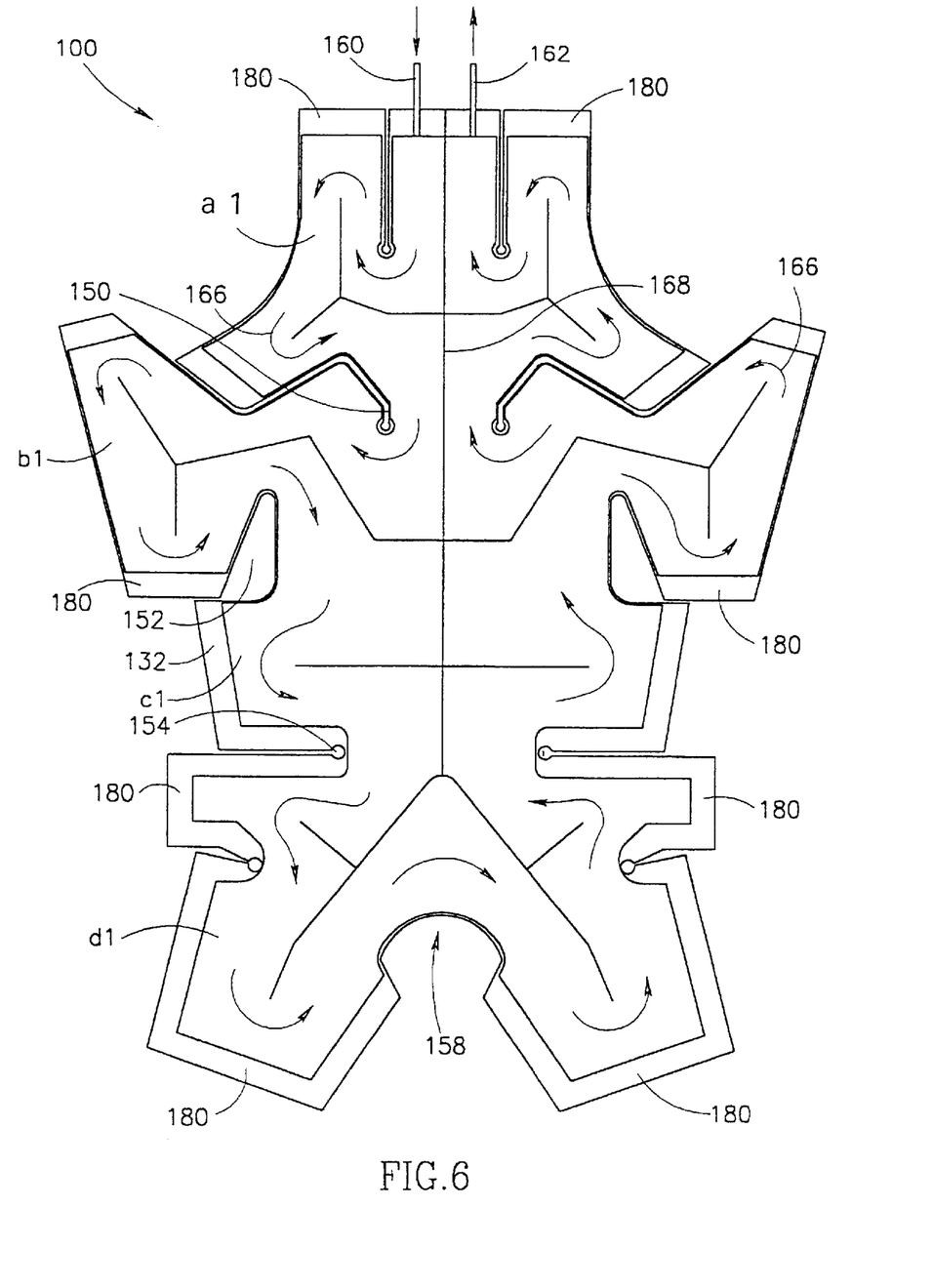
FIG. 6 is a top planar view of a garment in accordance with another embodiment of the invention.

The garment 20 may be provided with integral fastening means, e.g. hook and pile-type fasteners (see FIG. 4) or adhesive or pressure-sensitive patches (see FIG. 6). Alternatively, the fastening means may be applied prior to fitting the garment on the patient: for example, a two-sided patch may then be attached to the internal layer of the garment; separate straps or buckles, etc. may be added. All such fastening means are generally known per se.

Figure 3A:
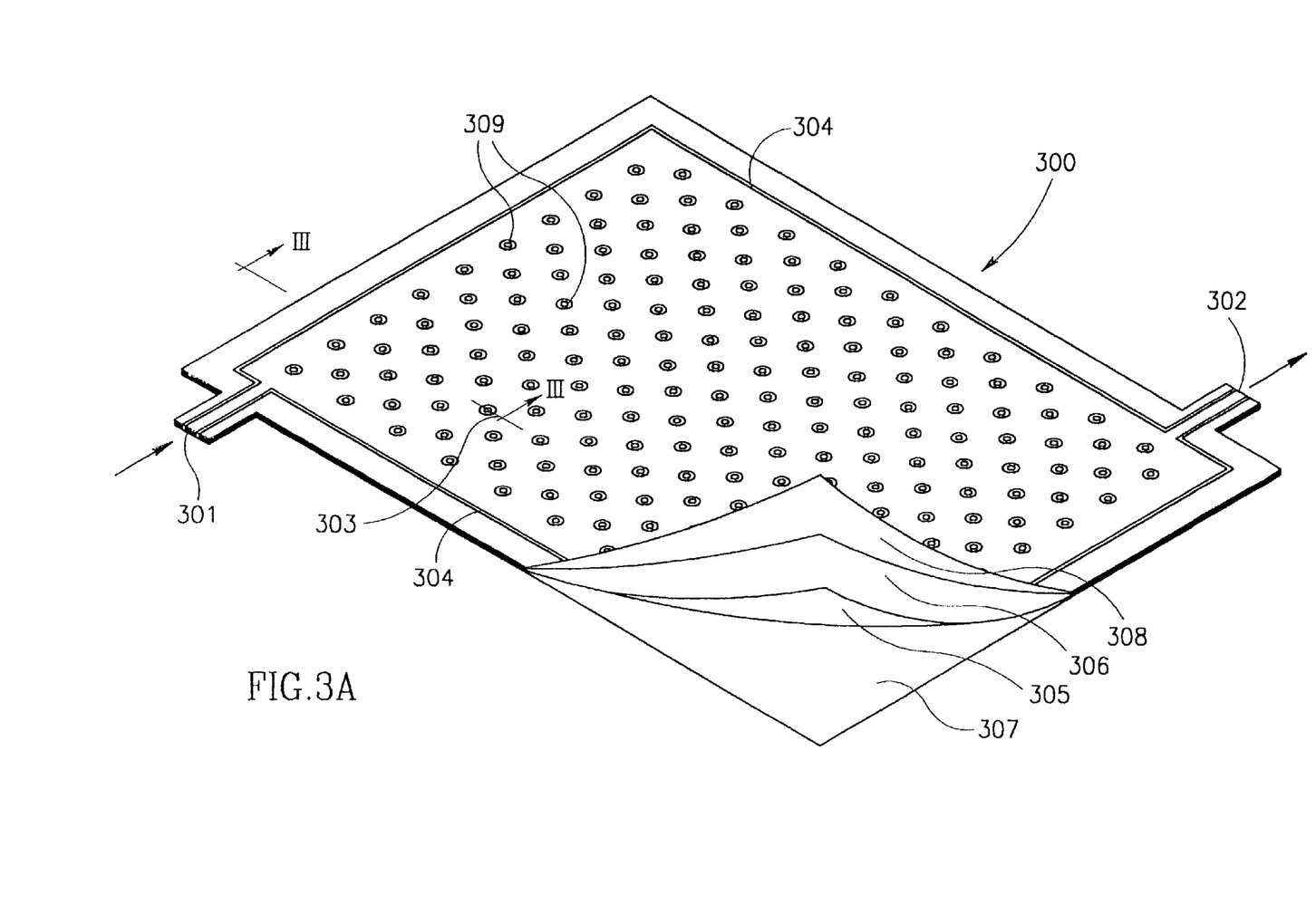
FIG. 3A shows an embodiment of a heat exchanger in accordance with an aspect of the invention, with one corner being opened to illustrate its four-layered construction. This heat exchanger is useful, in accordance with a preferred embodiment of the invention, in the garment of the invention.
Figure 3B:
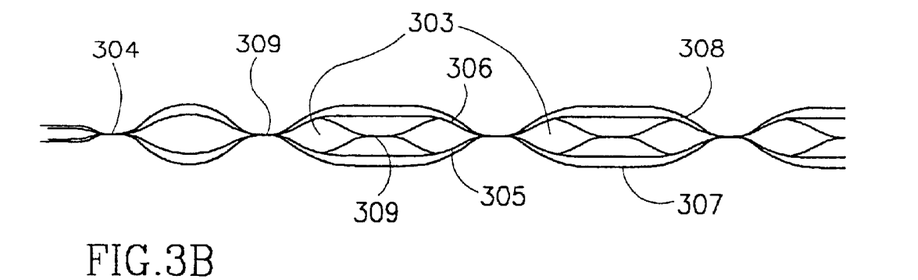
FIG. 3B is a cross-section through lines III—III in FIG. 3A.

Reference is now being made to FIGS. 3A and 3B showing a heat exchanger 300 having a fluid inlet 301 and a fluid outlet 302 for the transfer of heat exchange fluid through internal space 303 formed within the heat exchanger and confined by weld lines 304. Fluid inlet 301 and fluid outlet 302 are connected, respectively, to a fluid supply tube and to a fluid drainage tube which are in turn connected to a system which supplies the cooling fluid.

Fluid space 303 is defined between two fluid tight sheets or films 305 and 306 which are overlaid by respective outside layers 307 and 308. Sheets 305 and 306 are typically polyethylene sheets such as Metallocene PE (manufactured by Dow Elanco, USA) and layers 307 and 308 are made of non-woven polypropylene spunbond fabric of the characteristic weight of about 30–40 gm/m². As will, however, be appreciated, the external layers can be made to other specifications to meet any desired characteristics. They may have different characteristic weights, different textures, etc., to provide different levels of flexibility and insulation. The four layers are welded together, typically by R. F. (radio frequency) welding, at the edges 304 and at a plurality of weld points 309. The weld points 309 are typically arranged in an orderly fashion in an array, with the distance of well points being typically within the range of about 8 to about 20 mm from one another.

The overall rectangular design of the heat exchanger as seen in FIG. 3A is a mere example and the heat exchanger may be formed into various desired forms and shapes depending on the intended need. In accordance with one preferred embodiment of the invention, the body heat control garment in accordance with the invention is formed with a heat exchanger having the characteristics of the heat exchanger of the kind shown in FIGS. 3A and 3B. For such an application, the external non-woven spunbond fabric provides a physiologically compatible contact interface with the skin and furthermore, its somewhat hydrophilic properties permit absorption of liquids including sweat, blood, or other body fluids.

Figure 4:
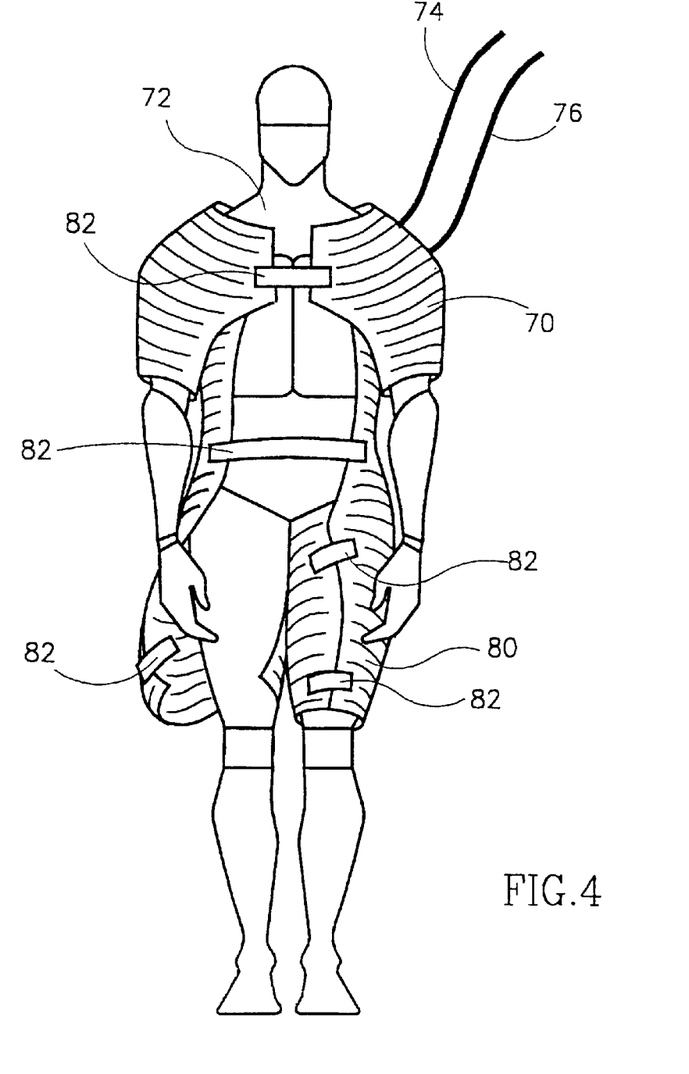
FIG. 4 is a schematic illustration of a garment in accordance with an embodiment of the invention applied to a patient.

A garment 70 in accordance with another embodiment, fitted over an individual 72 can be seen in FIG. 4. In this case, the fluid inlet and outlet 74, 76 are fitted in the garment in a shoulder section 78. In addition to shoulder section 78, the garment consists of a combined torso—thigh section 80. The fastening of the garment in an enveloping state is achieved by means of straps 82, particularly hook and pile-type fastening straps.

Figure 5:
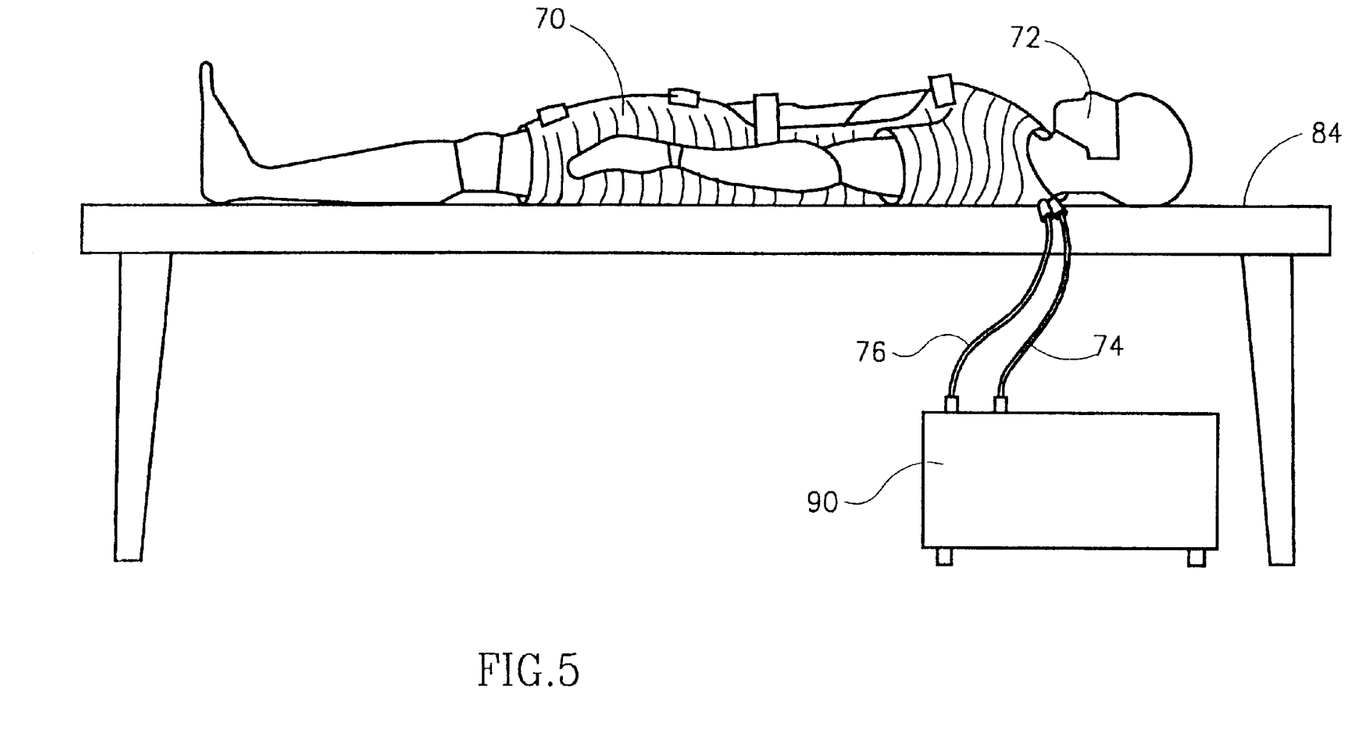
FIG. 5 is a side elevation of the patient with the garment of FIG. 3.

A side view of the patient with a garment of the embodiment of FIG. 4 can be seen in FIG. 5, with the patient placed on an operating table 84. Inlet and outlet pipes 74, 76 are connected to a heat transfer liquid control and circulation device 90. The fluid is typically a liquid such as water.

Reference is now being made to FIG. 6, showing a garment 100 in accordance with another embodiment of the invention. Although this garment has a somewhat different overall shape than the garment shown in FIG. 1, and accordingly functionally equivalent elements to those of FIG. 1 were given like reference numerals shifted by 100 (for example, element 168 in FIG. 6 is functionally equivalent to element 68 in FIG. 1), while elements marked by letters were marked by a corresponding letter with a "1" index (for example, element d1 in FIG. 6 is equivalent to element d in FIG. 1). The reader is referred to the description of FIG. 1 for proper explanation of the function of such elements.

Figure 7:
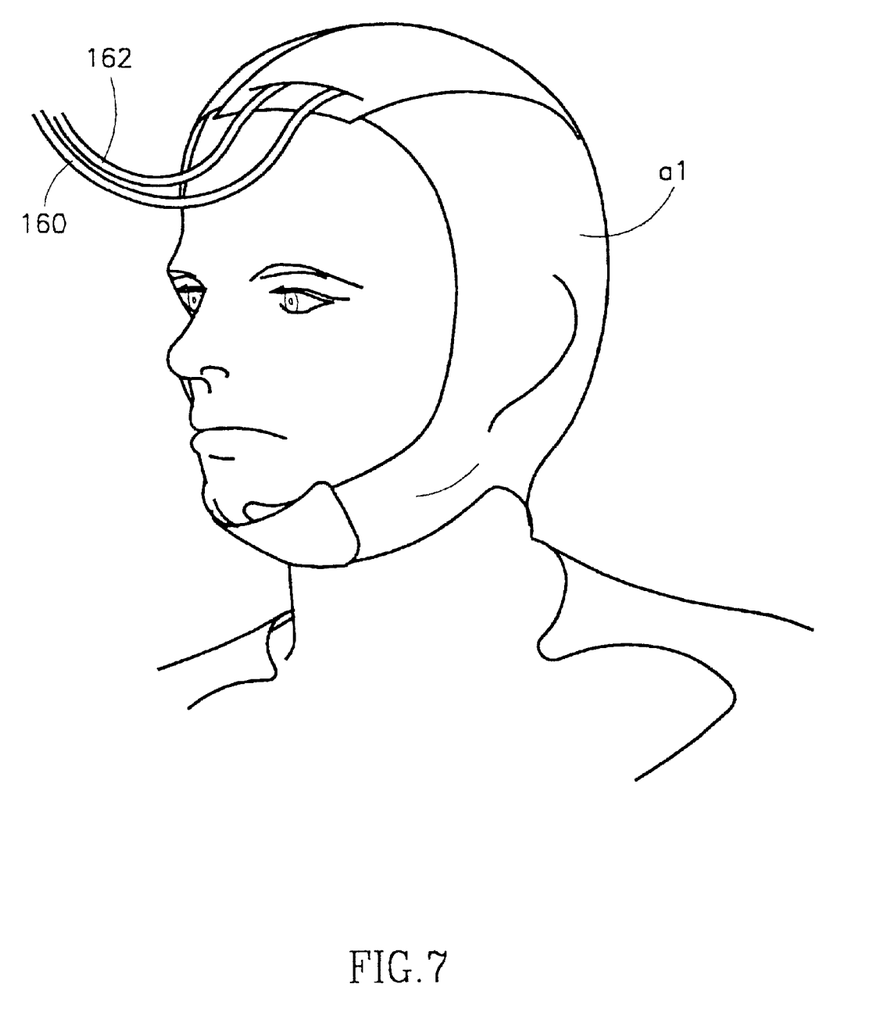
FIG. 7 shows the top portion of the garment as applied over a patient's head.

Garment 100 has two important differences from garment 20 of FIG. 1. For one, garment 100 does not have a section corresponding to Section e (intended for the shin) and furthermore, Section a1 is more extensive than Section a of garment 20 in that it is designed to substantially all non facial parts of the head. This novel feature is illustrated in FIG. 7.

The fixing of this garment is achieved, in this specific embodiment, by attachment patches 180 at edges of the garment. These attachment patches, typically an extension of the garment's external layer, may be covered by an adhesive material suitable for adherence to the skin or to an overlapping portion of the garment, or may be fitted with one attachment member of the hook and pile-type attachment couple, (e.g. VELCROTM-type attachment).

Figure 8:
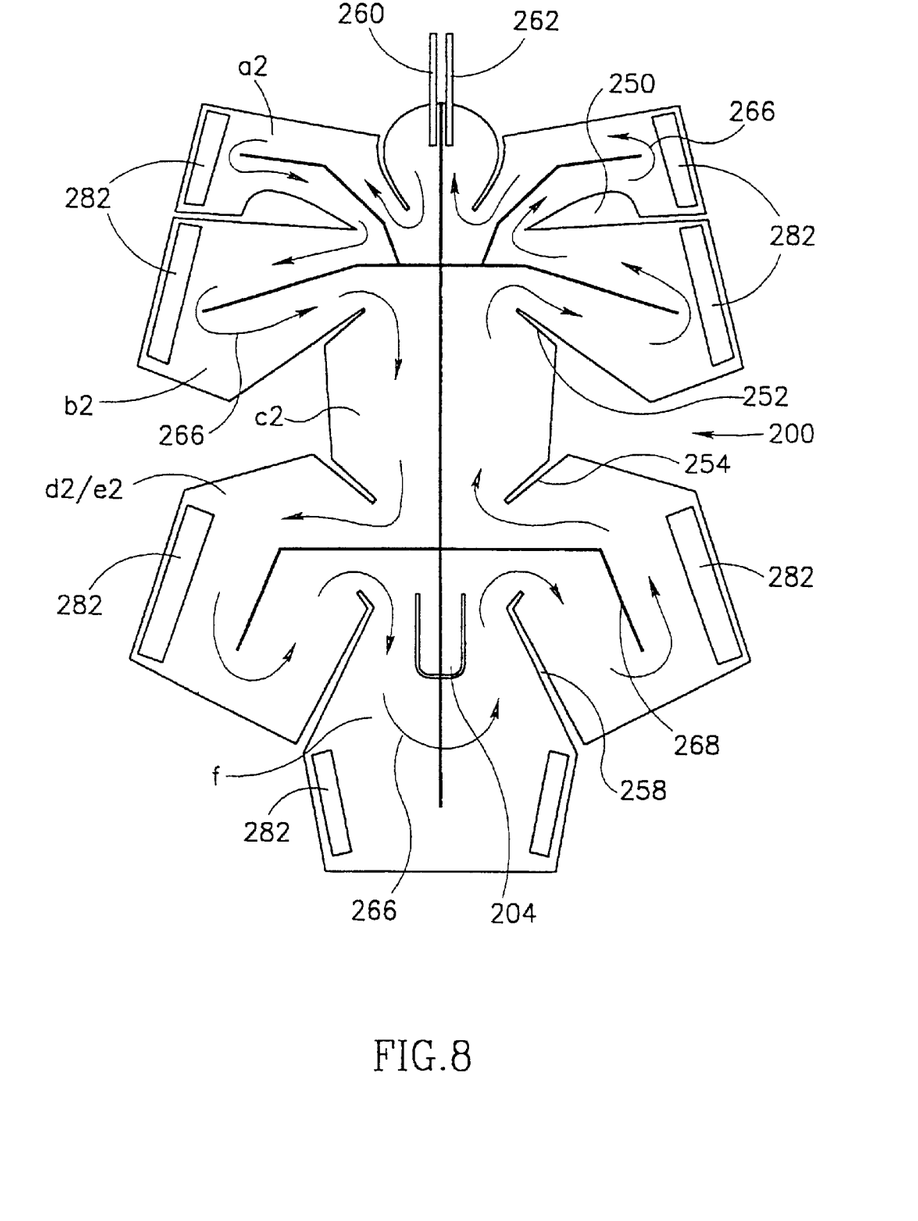
FIG. 8 shows a top elevational view of a garment in accordance with an embodiment of the invention adapted for use for dogs.

The garment in accordance with another embodiment of the invention is shown in FIG. 8. Garment 200 of this embodiment is designed for veterinary use, e.g. for a cat or a dog. Different elements of the garment of FIG. 8 being functional equivalents to those of the garment 20 of FIG. 1, have been given like reference numerals shifted by 200, while the elements marked by letters were marked by corresponding with a 2 index. The reader is referred to the description of FIG. 1 for proper explanation of the function of such elements.

The garment 200 of FIG. 8 is fitted with adhesive patches 282 whereby the garment can be fastened in the enveloping state to the animal's body, or to overlapping segments of the garment. The garment has a section f which may be forward folded over a lower abdominal part of the animal, and which is formed with a flap 204 which once folded forms an opening for the subject's tail.

As will be appreciated, the illustrated embodiments are but examples. The garment may be formed at a myriad of different shapes and sizes for different medical procedures and subjects.

What is claimed is:

1. A heat exchanger for use in controlling a subject's body temperature during a medical procedure, comprising:
   a) a flexible garment adapted for enveloping portions of the subject's body surface, the garment having dedicated sections for enveloping different body parts which comprise a torso section for enveloping substantial portions of the subject's torso and one or more of the individual's extremities;
   b) a fastening arrangement for retaining each section in an enveloping state;
   c) fluid-tight space defined between an internal, body-facing layer of the garment and an external layer and between fluid tight edges of the garment, said internal layer and said external layer each containing two faces, the faces of both layers lining said space being attached to one another along lines defining a flow path between at least one fluid inlet and at least one fluid outlet to permit flow of fluid from the at least one inlet to the at least one outlet throughout essentially the entire garment for effective heat transfer to or from all parts of the garment,
   said internal layer and said external layer being point welded to one another at a plurality of locations throughout the garment and comprise each an inner sub-layer having a thickness of about 20 to about 50 $\mu$m and an outer sub-layer comprised of non-woven material, all of the sub-layers are made of heat-weldable material, of which the two inner layers are fluid impermeable and define said fluid-tight space between them and the two outer layers are reinforcement, tear resistant layers which reinforce the structure of the garment to allow an internal fluid pressure of up to 3 atm without rupturing, each of said four layers being point welded to one another at radial locations throughout the garment.

2. A heat exchanger according to claim 1, wherein said space is a volume per unit area which is essentially the same throughout the garment.

3. A heat exchanger according to claim 1, wherein the welded points are separated from one another by about 8 to about 20 mm.

4. A heat exchanger according to claim 1, wherein the external layer is a non-woven spunbond fabric.

5. A heat exchanger according to claim 4, wherein the internal layer is made of polyethylene and the external layer of polypropylene.

6. A heat exchanger according to claim 1, wherein said garment comprises sections for enveloping portions of an individual's two legs and arms.

7. A heat exchanger according to claim 1, wherein the garment comprises a section for enveloping a substantial portion of non-facial parts of the individual's head.

8. A heat exchanger according to claim 1, for use in human medicine.

9. A heat exchanger according to claim 8, for use in controlling a patient's body temperature during surgery.

10. A heat exchanger according to claim 1, for use in veterinary medicine.

11. A heat exchanger according to claim 1, wherein, under an internal pressure of about 0.5–1.5 atmospheres, said space has an internal volume of about 1–3 liter/m$^2$ of garment surface.

12. A heat exchanger according to claim 11, wherein said space is about 1.7–2 liter/m$^2$ of garment surface.

13. A heat exchanger according to claim 1, wherein each section can be manipulated between an enveloping state and a non-enveloping state independently from other sections.

14. A garment according to claim 13, wherein the different sections are defined by emarginations in the garment's edges.

15. A heat exchanger according to claim 1, wherein flow-path defining lines are formed by welding.

16. A heat exchanger for use in the transfer of heat to or from a substrate, the heat exchanger being flexible such that it can assume the shape of said substrate and having a fluid-tight space defined within it for holding and transferring a heat-controlled fluid therethrough between a fluid inlet and a fluid outlet, the heat exchanger being characterized in that:

it comprises four, heat-weldable layers, of which two internal layers are made of a fluid-impermeable material and defining said space between them and of which the two external layers are made of a tear resistant material which reinforce the structure of the heat exchanger to improve the heat exchanger's ability to contain pressurized fluid within said space at a pressure of up to 3 atm without rupturing, said internal layers each having a thickness of about 20 to about 50 $\mu$m, and wherein said external layers are comprised of a non-woven material;

said four layers being point welded to one another at the edges, with the weld between the two internal layers being fluid tight, and are further welded to one another at a plurality of points throughout the heat exchanger.

17. A heat exchanger according to claim 16, wherein the external layers are made of a non-woven spunbound fabric.

18. A heat exchanger according to claim 17, wherein the internal layers are made of polyethylene and the external layers from a nonwoven spunbound polypropylene fabric.

19. A heat exchanger according to claim 16, wherein said space has a volume per unit area which is essentially the same throughout the heat exchanger.

20. A heat exchanger according to claim 16, wherein the welded points are separated from one another by about 8 to about 20 mm.

21. A method for controlling a subject's body temperature during a medical procedure, comprising enveloping portions of the subject's body surface with a heat exchanger according to claim 1 and allowing fluid flow between said at least one fluid inlet and said at least one fluid outlet, through said fluid-tight space forming part of said garment.

22. A method according to claim 21, wherein said fluid is a liquid.

23. A method according to claim 22, wherein said liquid is water.

24. A method according to claim 21, wherein said subject is under general anesthesia.

25. A method according to claim 21, wherein said medical procedure is surgery.

26. A method according to claim 25, wherein said medical procedure is open heart surgery.

27. A method according to claim 26, wherein the subject's body temperature is controllably reduced to about 35° C. during the open heart surgery and at the end of said surgery is increased back to normal body temperature.

* * * * *